(12) United States Patent
Hayes (10) Patent No.: US 7,533,514 B2
(45) Date of Patent: May 19, 2009

(54) METHOD AND APPARATUS FOR AUTOMATED HANDLING OF MEDICAL DEVICES DURING MANUFACTURE

(75) Inventor: Michaél Hayes, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 993 days.

(21) Appl. No.: 10/422,940

(22) Filed: Apr. 25, 2003

(65) Prior Publication Data

US 2004/0215347 A1    Oct. 28, 2004

(51) Int. Cl.
- B65B 11/50 (2006.01)
- B65B 5/00 (2006.01)
- A61L 33/00 (2006.01)
- A61K 9/00 (2006.01)
- B65D 81/02 (2006.01)

(52) U.S. Cl. ............... 53/397; 53/428; 53/450; 53/473; 53/131.1; 53/111 R; 427/2.24

(58) Field of Classification Search ............ 53/397, 53/450, 452, 428, 473, 111 R, 111 RC, 131.1; 427/2.1, 2.24, 446

See application file for complete search history.

(56) References Cited

U.S. PATENT DOCUMENTS

| | | | |
|---|---|---|---|
| 2,816,523 A | 12/1957 | Johnson | |
| 4,327,482 A * | 5/1982 | Araki et al. | 29/740 |
| 4,503,607 A * | 3/1985 | Asai et al. | 29/832 |
| 4,944,979 A * | 7/1990 | Gagliano et al. | 428/43 |
| 4,971,196 A * | 11/1990 | Kitamura et al. | 206/204 |
| 5,098,440 A | 3/1992 | Hillstead | |
| 5,318,181 A * | 6/1994 | Stover et al. | 206/459.1 |
| 5,554,181 A * | 9/1996 | Das | 623/1.12 |
| 5,682,731 A | 11/1997 | Althouse | |

(Continued)

FOREIGN PATENT DOCUMENTS

| EP | 0 221 001 | 5/1987 |
|---|---|---|
| EP | 0 249 763 | 12/1987 |
| EP | 0 575 719 A1 | 12/1993 |
| EP | 0 630 623 A2 | 12/1994 |
| EP | 0 683 625 A2 | 11/1995 |
| WO | WO 01/36273 A1 | 5/2001 |

OTHER PUBLICATIONS http://www.powerhousemuseum.com/hsc/cochlear/commercial.htm.*

(Continued)

*Primary Examiner*—Rinaldi I. Rada
*Assistant Examiner*—Gloria R. Weeks
(74) *Attorney, Agent, or Firm*—Kenyon & Kenyon LLP (57) ABSTRACT

Method and apparatus for automated handling of stents using tape and reel, tray or cassette processing equipment is provided to reduce stent and coating damage during production, storage and distribution, and to allow high volume processing. In the tape reel-based system, stents are fed into an automated tape assembly device for orientation and then fed between a carrier and cover tape. The tape assembly is gathered onto a reel and loaded into a receiver wherein stent-bearing tape is fed into an automated tape separator, and stents removed from the tape assembly are automatically mounted onto holders, which pass the stents through a coater. In the tray- or cassette-based system, the tape reel-based storage and feeding elements are replaced with tray- or cassette-based elements. Once coated, automated equipment removes the holders from the coated stents, and forwarded to alternative destinations, including storage or automated stent expansion balloon installation and crimping.

18 Claims, 3 Drawing Sheets

U.S. PATENT DOCUMENTS

| | | | |
|---|---|---|---|
| 6,063,139 A * | 5/2000 | Fukaya | 29/25.01 |
| 6,138,892 A * | 10/2000 | Kim et al. | 228/102 |
| 6,206,198 B1 * | 3/2001 | Troxtell et al. | 206/714 |
| 6,335,548 B1 * | 1/2002 | Roberts et al. | 257/98 |
| 6,517,889 B1 * | 2/2003 | Jayaraman | 427/2.24 |
| 6,527,863 B1 | 3/2003 | Pacetti et al. | |
| 6,537,459 B1 * | 3/2003 | Dufresne et al. | 216/8 |
| 6,629,993 B2 * | 10/2003 | Voinov | 623/1.15 |
| 6,723,373 B1 * | 4/2004 | Narayanan et al. | 427/2.25 |
| 6,972,054 B2 * | 12/2005 | Kerrigan | 118/500 |
| 2001/0001824 A1 * | 5/2001 | Wu | 606/108 |
| 2002/0026231 A1 * | 2/2002 | Shannon et al. | 623/1.13 |
| 2002/0103526 A1 * | 8/2002 | Steinke | 623/1.11 |
| 2004/0013792 A1 * | 1/2004 | Epstein et al. | 427/2.24 |
| 2004/0062875 A1 * | 4/2004 | Chappa et al. | 427/421 |
| 2005/0252805 A1 * | 11/2005 | Cervantes | 206/384 |
| 2006/0147611 A1 * | 7/2006 | Coye et al. | 427/2.1 |
| 2006/0216431 A1 * | 9/2006 | Kerrigan | 427/458 |

OTHER PUBLICATIONS http://www.finetech-medical.co.uk/documents/NMRC_EMPS04_TNI2.pdf.*
http://www.nexlogic.com/Medical-Bio-Medical.aspx.*
http://www.delphimedical.com/about/manufacturing/pcba/.*

* cited by examiner

METHOD AND APPARATUS FOR AUTOMATED HANDLING OF MEDICAL DEVICES DURING MANUFACTURE

FIELD OF THE INVENTION

The present invention generally regards the handling of medical devices, such as stents, during manufacture and application of therapeutic and/or protective coatings. More specifically, the present invention provides an apparatus and method for high volume automated device handling which minimizes manual handling-related damage to the individual work pieces and their coatings, and lowers production, storage and inventory costs.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location.

The term "therapeutic agent" as used herein includes one or more "therapeutic agents" or "drugs." The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act, through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The delivery of expandable stents is a specific example of a medical procedure that involves the deployment of coated implants. Expandable stents are tube-like medical devices, typically made from stainless steel, Tantalum, Platinum or Nitinol alloys, designed to be placed within the inner walls of a lumen within the body of a patient. These stents are typically maneuvered to a desired location within a lumen of the patient's body and then expanded to provide internal support for the lumen. The stents may be self-expanding or, alternatively, may require external forces to expand them, such as by inflating a balloon attached to the distal end of the stent delivery catheter.

Because of the direct contact of the stent with the inner walls of the lumen, stents have been coated with various compounds and therapeutic agents to enhance their effectiveness. These coatings may, among other things, be designed to facilitate the acceptance of the stent into its applied surroundings. Such coatings may also be designed to facilitate the delivery of one of the foregoing therapeutic agents to the target site for treating, preventing, or otherwise affecting the course of a disease or tissue or organ dysfunction.

Where the stent has been coated, care must be taken during its manufacture and delivery within the patient to ensure the coating is evenly applied and firmly adherent to the stent, and further that the coating is not damaged or completely removed from the implant during the deployment process. When the amount of coating is depleted the implant's effectiveness may be compromised and additional risks may be inured into the procedure. For example, when the coating of the implant includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the implant it can reduce or slow down the blood flowing past it, thereby, increasing the threat of thrombosis or, if it becomes dislodged, the risk of embolisms. In certain circumstances, the removal and reinsertion of the stent through a second medical procedure may be required where the coatings have been damaged or are defective.

During the manufacture and handling of stents and other coated medical devices, there are numerous opportunities for the devices and their coatings to be damaged. Many of these opportunities are associated with manual handling of the devices. For example, at a stent manufacturing facility, newly manufactured stents are commonly loaded manually by the manufacturer's employees into small transport boxes (approximately the size of a CD case) which contain slots or partitions for holding individual stents. This manual process is labor intensive and thus costly, and subjects the as-yet-uncoated stents to damage as they are selected from piles of stents, manipulated and aligned with the individual partitions in the transport boxes, and then dropped into their respective slots. Once the stents are packaged, they are typically transported to a second facility for application of a therapeutic coating, where they face the potential for further damage. In a typical stent handling scenario, the received stents are first individually removed from their partitions in the transport container, for example by use of a "syringe tip" style of grappling device. They are then manually placed onto stent coating holder fixtures for coating and manually removed from the holder fixtures after coating, followed by either manual placement of individual stents over stent expansion balloons or manual insertion into a storage container such as a vial for further transport and handling.

In addition to the substantial potential for damage to medical devices and their coatings during extensive manual handling in a typical manufacturing process, these labor-intensive processes have the further disadvantage that they do not permit high volume, low cost production of high quality coated medical devices.

In view of projected increases in the world-wide demand for coated medical devices such as such stents, there is a need for an apparatus process that will permit substantial increases in coated device production rates while decreasing device and device coating defect rates and production costs.

SUMMARY OF THE INVENTION

The present invention is directed to a method for overcoming the foregoing disadvantages. Unlike the labor-intensive manual handling processes commonly used in the medical device manufacturing and coating fields, in the electronics production industry it is well known to use automated component handling equipment such as tape and reel equipment or specially-adapted trays or cassettes (hereinafter trays) to permit automated collection and delivery of electronic components, such as chips, capacitors and transistors, in support of production processes such as populating a circuit board. The present invention provides a novel application of automated component handling systems to the demanding field of coated medical device production, specifically including automated handling of stents.

A first embodiment of the present invention is provided comprising an automated tape reel medical device stent handling system. In this embodiment, stents are fed into a stent-bearing tape assembly loading device which gently orients the stents into a desired orientation and then feeds them onto a continuous carrier tape at regular intervals. As the stents are placed on the carrier tape, a continuous cover tape is simultaneously placed over the stents, thereby sandwiching the stents between the carrier and cover tapes. The loaded stent tape is then gathered onto a tape reel for storage and transport. Optionally, prior to feeding the stents into the stent-bearing tape assembly loading device, the stents may have a stent holder, such as a formed nitinol wire, inserted into the center of the stent.

In a further development of this embodiment, the loaded stent-bearing tape reel is mounted on a tape reel receiver associated with an automated stent coating machine, such that as the stent-bearing tape is fed into the stent coating machine, the carrier tape and cover tape are separated from the stents and the stents are indexed into position in a moving queue. Once queued, an automated stent holder installer passes a stent holder through the longitudinal center of each stent, if a stent holder was not previously inserted in the stents prior to the stent-bearing tape assembly. The stent holder-mounted stents are then passed though an automated stent coating device and are coated by a stent coating applicator. Once coated, the stent holders are removed the stents, and the coated stents may be either directed toward storage or further processing. For example, the coated stents may be placed into individual storage containers, such as vials, or transported directly to an automated stent crimping machine for placement over, and crimping onto, stent expansion balloons. Automated packaging of the completed individual stent catheters may then be performed and the product distributed to medical facilities for implantation.

Another embodiment of the present invention is provided in the form of a stent-bearing tape reel handling apparatus, comprising a device for automated orientation and indexing of stents, a tape loading device for affixing stents between a continuous carrier tape and a continuous cover tape, and a tape reel upon which the assembled stent-bearing tape assembly is collected. A further development of this apparatus embodiment comprises use of stent-bearing tape feed equipment for automated feeding of the stent-bearing tape assembly into an automated stent coating apparatus, removal of the stents from the tape, placement of the stents on stent holders (if not previously placed on stent holders prior to assembly of the stent-bearing tape assembly) for continuous automated feeding of the stent holder-mounted stents into a stent coating applicator, and stent holder removal following stent coating application.

In yet a further embodiment, the automated handling of medical devices is conducted using trays or cassettes adapted to automated device pick-up and placement in lieu of the carrier tape and tape reel handling apparatus. In this embodiment, medical devices such as stents may be loaded by a device manufacturer onto trays or cassettes, for example, using automated vacuum stent pick-up equipment to avoid stent damage or contamination. The trays or cassettes may be uniquely identified by, for example, bar-coding (similar to bar-coding of loaded tape reels). The trays or cassettes may then be subsequently loaded into an automated feeding apparatus on a device coating machine capable of automated pick-up of the devices directly from an opened tray or cassette. After the devices are coated, they may also be placed back into the tray or cassette by automated device handling machinery.

In each of the foregoing embodiments, it is presumed that any prior stent processing operations, such as individual stent weighing and barcoding for identification, have been completed prior to stent-bearing tape assembly. Alternatively, additional stent processing steps may be performed after the stents have been removed from stent-bearing tape assembly, but before their introduction into the stent coating application apparatus.

Each of the foregoing embodiments of the present invention solve the prior problems of manual work piece handling during the medical device manufacture and coating processes by permitting high-speed automated handling of the work pieces. Such a production process minimizes handling-induced device and device coating damage, increases production rates, and lowers production costs by eliminating costly labor-intensive manual handling of the individual work pieces. Further, because the medical devices arriving at a coating facility do not require additional manual handling prior to introduction to the coating applicators, the use of a device tape reel system supports "lean" or "just-in-time" manufacturing processes, lowering inventory-related production costs.

DETAILED DESCRIPTION

Figure 1:
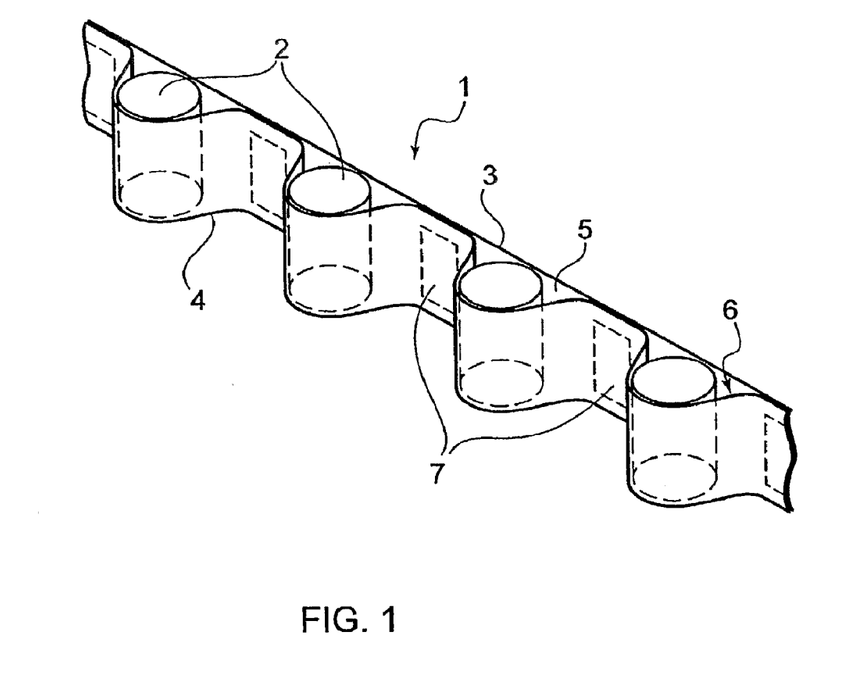
FIG. 1 is an oblique schematic view of an embodiment of a stent-bearing tape assembly in accordance with the present invention.

The present invention is directed to an apparatus and method for overcoming the foregoing disadvantages. FIG. 1 is a schematic illustration of an embodiment of a stent-bearing tape assembly 1 in accordance with the present invention. In this embodiment, a plurality of stents 2 have been placed in contact with a continuous carrier tape 3, and covered with a continuous cover tape 4 to form stent-bearing tape assembly 1. Either or both of carrier tape 3 or cover tape 4 may have an adhesive, such as a pressure-sensitive adhesive, on their respective tape faces 5, 6. The adhesive may be located on the carrier tape 3 and/or cover tape 4 at intervals along the tape, shown in FIG. 1 as regions 7. As the stents 2 are placed between carrier tape 3 and cover tape 4, the tapes are pressed together in the regions, such that the stents 2 are held between the tapes in non-adhesive bearing regions, thus avoiding adhesive contamination of stents. Other adhesive locations on the tapes may also be utilized as long as the arrangements ensure the stents 2 are not contacted by the adhesive and remain held between the tapes in the desired orientation. For example, the stent-bearing tape assembly may include tapes of sufficient width to meet one another at the top and bottom of the tape assembly and thereby enclose the entrained stents to avoid environmental contamination of the stents during handling.

Stent-bearing tape assembly 1 may be formed using adaptations of tape assembly equipment well known in the electronics manufacturing field, such as the Model RT-100 Radial Taping Machine available from Illinois Components, Inc. of Downers Grove, Ill., USA. In order to employ such tape assembly equipment, it must be suitably adapted for use with stents, which may be damaged by handling stresses that electronic components could survive during tape assembly. For example, any portion of the tape assembly equipment that applies a radial load on the work piece must be adjusted to ensure that no load which could deform a stent is applied.

Figure 2:
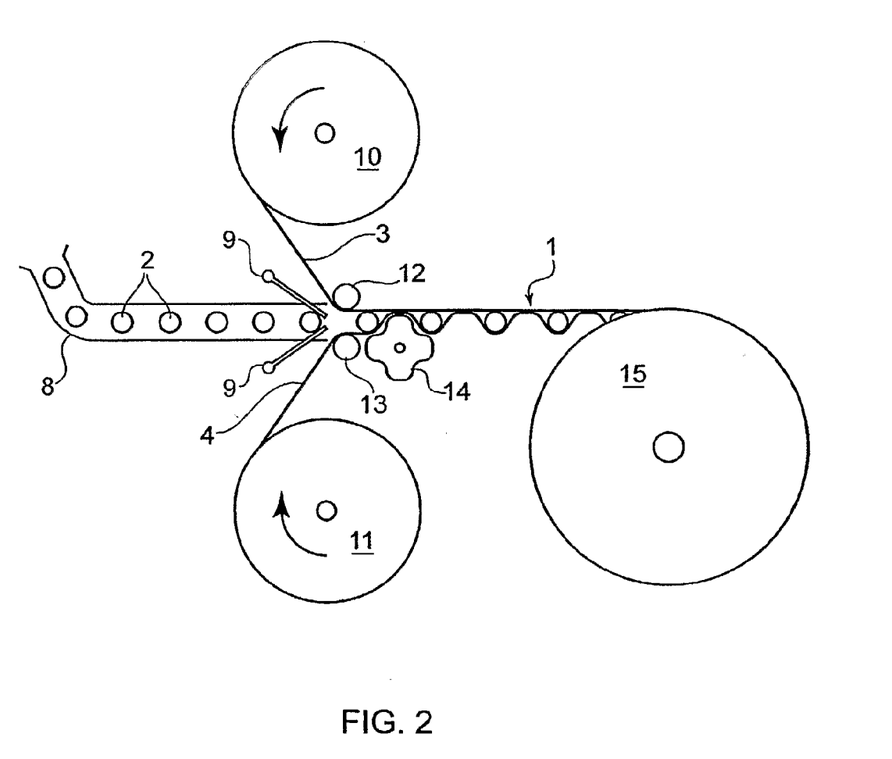
FIG. 2 is a schematic view of an embodiment of automated equipment assembling a stent-bearing tape assembly in accordance with the present invention.

A schematic illustration of the function of such tape assembling equipment is shown in FIG. 2. In this illustration, a plurality of stents 2 are received, for example from the output of a stent manufacturing process, into a stent orienting and indexing apparatus (not shown) which processes the stents into a desired orientation by well-known sorting techniques, such as the combination of vibration and appropriately sized and shaped guide rails, or "pick-and-place" equipment. The oriented stents are then delivered by a conveying means 8, such as a conveyor belt or a gravity chute, to a tape assembly station. Alternatively, before entering the tape assembly station, the stents may first be subjected to other processing such as individual stent weighing. The alternative processing may further include removal of individual stents from the conveying means, such as by use of a vacuum handling equipment, followed by their return to the conveying means in the desired orientation.

Further processing may also take place on the conveying means, such as insertion of self-retaining shaped-wire stent holders axially through the stents to facilitate subsequent stent processing after the stents are removed from the stent-bearing tape assembly. An example of such a wire stent holder is disclosed in The exemplary stent holder in the present embodiment is a wire with at least two pre-formed stent-contacting bends and two physical states, as disclosed in U.S. patent application Ser. No. 10/198,094 filed Jul. 19, 2002.

When this stent holder wire is in a first state, it contracts and the bends expand radially until they contact the inner surface of stent 2. When in a second state, the wire bends elongate in the axial direction of the wire at least until the stent can pass over the wire without contacting the bends. Examples of the two states of the wire stent holder include applied and released longitudinal tension, or high and low wire temperatures (the latter resulting from, for example, environmental heating or cooling of the wire or application or removal of a resistive heating electric current through the wire).

Once the stents enter the tape assembly station, indexing equipment 9 controls the release of stents in the desired orientation at predetermined intervals to meet carrier tape 3 being fed from carrier tape reel 10 and cover tape 4 being fed from cover tape reel 11. In this embodiment, as carrier tape 3, cover tape 4 and stents 2 meet, guide rollers 12, 13 guide the tapes and stents toward assembly roller 14. As the tapes and stents pass assembly roller 14, the lobes on roller 14 urge cover tape 4 into contact with carrier tape 3 in adhesive regions 7 in order to join the tapes. The lobes on assembly roller 14 are sized to permit the indexed stents to pass roller 14 underneath cover tape 4 without the application of compressive forces from the roller to the stents. A tape tensioner (not shown) maintains sufficient tension on cover tape 14 to ensure that cover tape 4 is affixed to carrier tape 3 without excess slack, i.e., such that the cover tape applies sufficient normal force to the stents to ensure they remain held between the tapes without application of adhesive to the stents. The pressure applied by guide rollers 12, 13, assembly roller 14 and the cover tape tensioner must be regulated to avoid applying pressure high enough to crush or otherwise damage the stents.

Once assembled, stent-bearing tape assembly 1 may be gathered onto a take-up reel 15. After filling, reel 15 may be removed from the tape assembly equipment and transported to interim storage or to a further stent processing facility, such as stent coating facility. The loaded reel 15 may also be provided a label such as a bar-code label to enhance inventory control and batch tracking. In an alternative embodiment, if stent-holder wires have not previously been inserted through the stents, the wired may be inserted through the indexed and captured stents following tape assembly but before take-up of the assembled stent-bearing tape onto reel 15.

Figure 3:
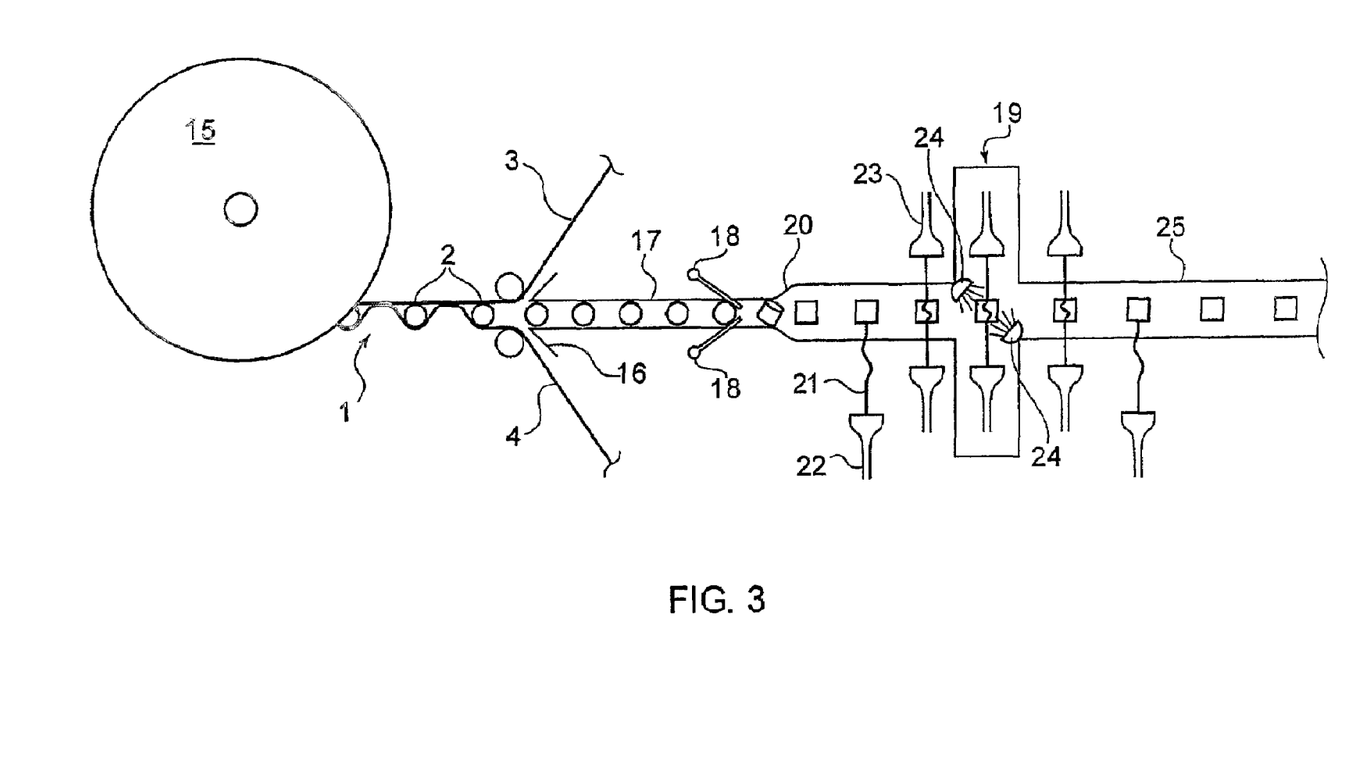
FIG. 3 is a schematic view of an embodiment of an automated stent coating process adapted to use of a stent-bearing tape assembly in accordance with the present invention.

A schematic illustration of the use of a stent-bearing tape assembly in an automated stent coating facility is shown in FIG. 3. In this embodiment, stent-bearing tape assembly reel 15 may be placed on a tape reel receiver (not shown), and stent-bearing tape assembly 1 fed into an automated tape separating device 16. Tape separating device 16, show schematically in FIG. 3, may separate carrier tape 10 and cover tape 4 from the plurality of stents 2. If the stents previously received stent-holding wires prior to or during the assembly of the stent-bearing tape assembly, automated stent handling equipment may engage the stent holders as the stents are released from the stent-bearing tape assembly and transport the holder-mounted stents directly downstream for further processing. If the stents did not previously receive stent holders, stent holders may be inserted into the stents as the stent-bearing tape assembly 1 is unrolled from reel 15. Alternatively, the stents may be placed on stent holders after the stents have been separated from the tape assembly. For example, as shown in FIG. 3, after separation from the tape assembly, the stents may proceed down a conveying means 17, such as a conveyor belt or a gravity chute, until the stents reach indexer 18. Indexer 18 controls the release of stents 2 in the desired orientation at predetermined intervals to be processed through stent coating applicator 19.

In this embodiment, as the stents 2 are released by indexer 18, they may be reoriented in transition zone 20 into a position amenable for insertion of a stent coating holder 21, which may be a stent as disclosed in U.S. patent application Ser. No. 10/198,094. An automated stent holder inserting machine may insert stent holder wire 21 through a on a continuous flow basis in the following manner. As the plurality of stents 2 emerge from transition zone 20, each of a plurality of lower stent holder clamps 22 acts as a stent holder inserter to guide a stent holder wire 21 into the longitudinal center of the next successively presented stent 2. As the automated stent feeding process continues, lower stent holder clamp 22 guides stent holder wire 21 through the center of stent 2 until the free end of stent holder wire 21 is captured by upper stent holder clamp 23. Once captured by upper stent holder clamp 23, stent holding wire 21 is caused to transition into its second state (i.e., elongated sufficiently to not contact the inner surface of a stent), then stent holding wire 21 is further moved through the center of stent 2 until the wire's bends are within the stent. Stent holder wire 21 is then caused to transition from its second state to its first state to apply a retaining and positioning force on stent 2. Stent 2 may then be lifted away from conveying means 17 and into automated stent coating applicator 19. In the present embodiment, the second state is actuated by the application of longitudinal tension to the wire by lower stent holder clamp 22 and upper stent holder clamp 23, and the first state is achieved by releasing the longitudinal tension.

Following application of a stent coating to stent 2, illustrated in the present embodiment by exemplary coating spray nozzles 24, and elapse of sufficient coating drying time, the coated stent 2 may be placed on a second conveying means 25. As the plurality of coated stents 2 proceed along conveying means 25, automated stent holder release is performed in the following manner. Stent holding wire 21 is caused to transition from its first state to its second state in order to release coated stent 2 from contact with the wire's bends. Stent holder wire 21 is next pulled axially through coated stent 2 a distance sufficient to draw the wire's bends clear of the stent, at which point the end of stent holder wire 21 held by upper stent holder clamp 23 is released, permitting stent holder wire 21 to be drawn completely out of the center of coated stent 2 by lower stent holder clamp 22 functioning as a stent holder remover.

The plurality of coated stents may then continue to be transported by conveying means 25 to any of a number of destinations for subsequent processing (not illustrated). For example, the coated stents may be collected by automated packaging machinery and placed in to individual storage containers, such as vials and multi-compartment boxes. Alternatively, the plurality of coated stents may be conveyed to further manufacturing stations or facilities for further processing, such as to an automated stent expansion balloon catheter assembly station, wherein the stents are placed over a stent expansion balloon and crimped over the balloon. In yet another alternative, the coated stents may be collected into a coated stent-bearing tape assembly and reel for storage or further processing.

In a further embodiment of the present invention, rather than creating stent-bearing tapes and loading the tapes onto reels, the stents may be loaded by automated sorting and orienting equipment adapted to place the newly-manufactured stents into trays or cassettes specially adapted to hold and protect the stents during transport and handling. Preferably, the loading of the stents into trays or cassettes is performed in the manufacturer's facility to minimize handling and consequent opportunities for damage. The loaded stent-bearing trays or cassettes may be covered to protect the stents, and then may, for example, be placed into storage for later processing, or transported for further processing. For stent coating, the trays or cassettes may be delivered for feeding to automated stent coating equipment similar to that described above, where the stent coating equipment is provided with tray or cassette feeding apparatus adapted to receive the trays or cassettes and perform automated stent pick-up, orientation and insertion into the stent coating apparatus. An example of a tray or cassette receiving apparatus which may be adapted for use in handling stent-bearing trays or cassettes, as well as being adaptable for receiving stent-bearing tape reels, is the Model MPA-V Multifunctional Placement Machine offered by Panasonic Factory Automation Company USA of Franklin Park, Ill. Further, the trays or cassettes may be re-used by automated loading equipment to receive the coated stents as they are removed from the stent coating equipment.

As will be apparent to one of skill in the art, the foregoing embodiments of the present invention solve the prior problems of medical device and device coating damage and high labor costs arising from multiple manual work piece handling operations during stent manufacture, storage, coating, product assembly and distribution processes. The present invention further enables decreased product defect rates, reduced requirements for custom manual medical device handling tooling, and increased production rates not possible with the prior manual handling of individual work pieces. Moreover, because the medical devices arriving at a coating facility do not require additional manual handling prior to introduction to the coating applicators, the use of a device tape reel system supports "lean" or "just-in-time" manufacturing processes, lowering inventory-related stent production costs. The use of trays or cassettes in this embodiment of the present invention provides the advantages of permitting convenient visual inspection of the loaded devices (for example, by viewing stents through transparent tray covers), inventory and batch control labeling, and space-efficient stacking and storage.

While the present invention has been described with reference to what are presently considered to be preferred embodiments thereof, and with particular emphasis on stent processing and coating, it is to be understood that the present invention is not limited to the disclosed embodiments or constructions. On the contrary, the present invention is intended to cover the automated handling of a variety of medical devices which require coating or similar high-volume automated processing, as well as various modifications and equivalent arrangements to the processing, such as the substitution of a different stent holder design, such as a center rod, a tube or an external holder for the stent holding wire in the described embodiments. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A method for automated work piece coating, comprising:
   loading a tape reel containing a work piece-bearing tape assembly onto a work piece-bearing tape receiver, wherein the work piece-bearing tape assembly includes a plurality of work pieces held between a continuous carrier tape and a continuous cover tape;
   feeding the work piece-bearing tape assembly from the work piece-bearing tape receiver into an automated tape assembly separator;
   separating the plurality of work pieces from the carrier tape and the cover tape, wherein the plurality of work pieces is maintained in a desired orientation following separation;
   mounting at least one of the plurality of work pieces onto a central element of one of a plurality of individual work piece holders using an automated work piece holder mounting device, such that the central element passes longitudinally through at least one of the plurality of work pieces;
   feeding the work piece holder-mounted plurality of work pieces through an automated work piece coating applicator; and
   removing the plurality of work pieces from the plurality of work piece holders after application of a work piece coating using an automated work piece holder removal device;
   wherein the work pieces are stents.

2. The method of claim 1, further comprising, after the step of removing the work piece holders, the step of:
   loading the plurality of work pieces into a plurality of coated work piece holding containers using an automated coated work piece holding container loading device.

3. The method of claim 1, further comprising, after the step of removing the work piece holders, the steps of:
   feeding individual work pieces from the plurality of work pieces at predetermined intervals onto a continuous coated work piece carrier tape using an automated work piece feeder;
   applying a continuous coated work piece cover tape over the work pieces on the coated work piece carrier tape to form a coated work piece-bearing tape assembly, wherein the plurality of work pieces are held between the coated work piece carrier tape and the coated work piece cover tape; and
   gathering the coated work piece-bearing tape assembly onto a coated work piece tape reel.

4. The method of claim 1, wherein
   the central element is a wire,
   when the wire is in a first state, the wire has at least two bends substantially transverse to a longitudinal axis of the element, and a sum of a width of one of the at least two bends on a first side of the wire and a width of another of the at least two bends on a second side of the wire substantially opposite the first side is greater than an inner diameter of the stents, and
   when the wire is in a second state, the at least two bends are reduced in width such that the wire may pass through the stent without contacting an inner surface of the stent after application of the stent coating.

5. A method of claim 4, wherein the step of mounting the stents on the work piece holders using the automated work piece holder mounting device comprises:
   passing a first end of the wire in the first state longitudinally through the at least one stent;
   causing the wire to be placed into the second state;
   placing the at least one stent over at least two bends; and
   causing the wire to be in the first state such that the inner surface of the at least one stent is contacted by the wire at at least two points.

6. The method of claim 5, wherein the first state is a state in which an axial tension load is not applied to the wire, and the second state is a state in which an axial tension load is applied to the first end of the wire and a second end of the wire.

7. The method of claim 6, wherein the first state is a state in which a temperature of the wire is at least high enough to cause the at least two bends in the wire to reach the inner surface of the at least one stent, and the second state is a state in which the temperature of the wire is at least low enough to cause the at least two bends to not contact the inner surface of the at least one stent.

8. The method of claim 1, further comprising, before the step of loading a tape reel containing a work piece-bearing tape assembly onto a work piece-bearing tape receiver, the steps of:
   orienting a plurality of work pieces in a desired direction with an automated work piece orienting device;
   feeding individual work pieces from the plurality of oriented work pieces at predetermined intervals onto a continuous carrier tape in a desired orientation using an automated work piece feeder;
   applying a continuous cover tape onto the work pieces on the carrier tape to form a work piece-bearing tape assembly, wherein the plurality of work pieces are held between opposing faces of the carrier tape and the cover tape; and
   gathering the work piece-bearing tape assembly onto a tape reel.

9. The method of claim 8, wherein at least one of the carrier tape and the cover tape includes a pressure-sensitive adhesive on a face facing the work pieces.

10. The method of claim 1, wherein the medical devices are implantable.

11. A method for automated work piece coating, comprising:
   loading a tape reel containing a work piece-bearing tape assembly onto a work piece-bearing tape receiver, wherein the work piece-bearing tape assembly includes a plurality of work pieces held between a continuous carrier tape and a continuous cover tape;
   feeding the work piece-bearing tape assembly from the work piece-bearing tape receiver into an automated tape assembly separator;
   separating the plurality of work pieces from the carrier tape and the cover tape, wherein the plurality of work pieces is maintained in a desired orientation following separation;
   mounting at least one of the plurality of work pieces onto one of a plurality of individual work piece holders using an automated work piece holder mounting device;
   feeding the work piece holder-mounted plurality of work pieces through an automated work piece coating applicator;
   removing the plurality of work pieces from the plurality of work piece holders after application of a work piece coating using an automated work piece holder removal device; and
   after the removing step, the steps of:
      placing each of the plurality of stents concentrically over one of a plurality of stent expansion balloons using an automated stent placement device; and
      crimping each of the plurality of stents onto the stent expansion balloon over which it was placed using an automated stent crimping device;
   wherein the work pieces are stents.

12. A method for automated work piece coating, comprising:
   loading a work piece holding container onto a work piece holding container receiver, wherein the work piece holding container includes a plurality of work pieces held in work piece receiving positions and maintained in a first desired orientation;
   extracting individual work pieces from the work piece holding container using an automated work piece extracting device;
   feeding the work pieces extracted from the work piece holding container into a work piece coating machine at a desired interval and in a second desired orientation;
   individually mounting the plurality of work pieces onto a central element of a plurality of individual work piece holders using an automated work piece holder mounting device, wherein at least one of the plurality of work pieces is mounted on each work piece holder, such that the central elements passes longitudinally through at least one of the plurality of work pieces;
   feeding the work piece holder-mounted plurality of work pieces through an automated work piece coating applicator; and
   removing the plurality of work pieces from the plurality of work piece holders after application of a work piece coating using an automated work piece holder removal device;
   wherein the work pieces are stents.

13. The method of claim 12, further comprising, after the step of removing the work piece holders, the step of:
   loading the plurality of work pieces into a plurality of coated work piece holding containers using an automated coated work piece holding container loading device.

14. The method of claim 12, wherein
   the central element is a wire,
   when the wire is in a first state, the wire has at least two bends substantially transverse to a longitudinal axis of the element, and a sum of a width of one of the at least two bends on a first side of the wire and a width of another of the at least two bends on a second side of the wire substantially opposite the first side is greater than an inner diameter of the stents, and
   when the wire is in a second state, the at least two bends are reduced in width such that the wire may pass through the stent without contacting an inner surface of the stent after application of the stent coating.

15. A method of claim 14, wherein the step of mounting the stents on the stent holders using the automated stent holder mounting device comprises:
   passing a first end of the wire in the first state longitudinally through the at least one stent;
   causing the wire to be placed into the second state;
   placing the at least one stent over at least two bends; and
   causing the wire to be in the first state such that the inner surface of the at least one stent is contacted by the wire at at least two points.

16. The method of claim 15, wherein the first state is a state in which an axial tension load is not applied to the wire, and the second state is a state in which an axial tension load is applied to the first end of the wire and a second end of the wire.

17. The method of claim 16, wherein the first state is a state in which a temperature of the wire is at least high enough to cause the at least two bends in the wire to reach the inner surface of the at least one stent, and the second state is a state in which the temperature of the wire is at least low enough to cause the at least two bends to not contact the inner surface of the at least one stent.

18. A method for automated work piece coating, comprising:
   loading a work piece holding container onto a work piece holding container receiver, wherein the work piece holding container includes a plurality of work pieces held in work piece receiving positions and maintained in a first desired orientation;

extracting individual work pieces from the work piece holding container using an automated work piece extracting device;

feeding the work pieces extracted from the work piece holding container into a work piece coating machine at a desired interval and in a second desired orientation;

individually mounting the plurality of work pieces onto a plurality of individual work piece holders using an automated work piece holder mounting device, wherein at least one of the plurality of work pieces is mounted on each work piece holder;

feeding the work piece holder-mounted plurality of work pieces through an automated work piece coating applicator;

removing the plurality of work pieces from the plurality of work piece holders after application of a work piece coating using an automated work piece holder removal device; and after the step of removing the work piece holders, the steps of:

placing each of the plurality of stents concentrically over one of a plurality of stent expansion balloons using an automated stent placement device; and crimping each of the plurality of stents onto the stent expansion balloon over which it was placed using an automated stent crimping device;

wherein the work pieces are stents.

* * * * *